(12) United States Patent  (10) Patent No.: US 8,071,392 B2
Matsukawa  (45) Date of Patent: Dec. 6, 2011

(54) MASS SPECTROMETRIC ANALYSIS OF PROTEINS USING STABLE ISOTOPES OF PYRYLIUM DERIVATES AS LABELS

(75) Inventor: Shigeru Matsukawa, Fukui (JP)

(73) Assignees: National University Corporation University of Fukui, Fukui (JP); Taiyo Nippon Sanso Corporation, Tokyo (JP)

( * ) Notice: Subject to any disclaimer, the term of this patent is extended or adjusted under 35 U.S.C. 154(b) by 0 days.

(21) Appl. No.: 12/452,233

(22) PCT Filed: Jun. 19, 2008

(86) PCT No.: PCT/JP2008/061243
§ 371 (c)(1),
(2), (4) Date: Mar. 19, 2010

(87) PCT Pub. No.: WO2008/156139
PCT Pub. Date: Dec. 24, 2008

(65) Prior Publication Data
US 2010/0190261 A1    Jul. 29, 2010

(30) Foreign Application Priority Data
Jun. 21, 2007  (JP) .................. 2007-164249

(51) Int. Cl.
*G01N 24/00* (2006.01)
*G01N 33/00* (2006.01)
(52) U.S. Cl. ............... 436/173; 436/86; 436/89; 436/90
(58) Field of Classification Search .................. None
See application file for complete search history.

(56) References Cited

U.S. PATENT DOCUMENTS
2007/0099304 A1    5/2007    Puente et al.

FOREIGN PATENT DOCUMENTS
| EP | 1 696 230 | 8/2006 |
| JP | 2003-107066 | 4/2003 |
| JP | 2005-181011 | 7/2005 |
| JP | 2007-127631 | 5/2007 |

(Continued)

OTHER PUBLICATIONS

International Search Report issued Jul. 29, 2008 in International (PCT) Application No. PCT/JP2008/061243.

(Continued)

*Primary Examiner* — Yelena G Gakh
(74) *Attorney, Agent, or Firm* — Wenderoth, Lind & Ponack, L.L.P.

(57) ABSTRACT

The present invention provides a protein analysis method using a combination of two or more kinds of stable isotopes of a compound represented by the formula (I):

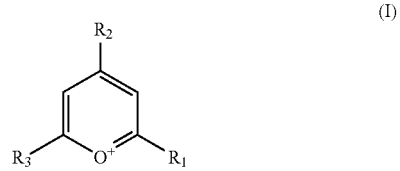

wherein $R_1$, $R_2$ and $R_3$ are the same or different and each is hydrogen, halogen or alkyl, or a salt thereof, as a labeling compound to produce a difference in the mass of the same kind of protein contained in each sample.

7 Claims, 4 Drawing Sheets

FOREIGN PATENT DOCUMENTS

WO          00/11208          3/2000

OTHER PUBLICATIONS

Douglas B. Craig et al., "Determination of picomolar concentrations of proteins using novel amino reactive chameleon labels and capillary electrophoresis laser-induced fluorescence detection", Electrophoresis, vol. 26, Issue 11, pp. 2208-2213, May 9, 2005.

Ion Ghiviriga et al., "Rotation Barriers in Pyridinium Salts Depend on the Number of Available Ground State Conformations", Croatica Chemica Acta, vol. 77, No. 1-2, pp. 391-396, 2004.

Michael B. Goshe et al., "Stable isotope-coded proteomic mass spectrometry", Current Opinion in Biotechnology, vol. 14, No. 1, pp. 101-109, Feb. 2003.

Form PCT/IB/338 together with translation of International Preliminary Report on Patentability in International (PCT) Application No. PCT/JP2008/061243.

MASS SPECTROMETRIC ANALYSIS OF PROTEINS USING STABLE ISOTOPES OF PYRYLIUM DERIVATES AS LABELS

TECHNICAL FIELD

The present invention relates to a method of analyzing a protein. More particularly, the present invention relates to a method including comparing two or more kinds of protein-containing samples using a mass spectrometer, and analyzing the quantitative ratio of the same kind of protein contained in each sample. The present invention also provides a reagent kit useful for the analysis of a protein using a mass spectrometer.

BACKGROUND ART

With the progress of genome structure analysis of various organisms, primary structure information of candidate proteins that are predicted to act in the cell has been accumulated. However, it should be noted that the protein information extracted from genetic information is merely information, and is not an actual substance. In fact, cells and tissues are said to translate only a part of the whole genetic information in the nucleus, and the kind thereof varies depending on the origin of cells and tissues. Moreover, it seems that the quality and quantity of the protein to be expressed change from moment to moment during the development to differentiation process. In cells, moreover, a variety of proteins interact in a complicated manner to maintain life activity of the cells. It is desired that the functional analysis of gene proceed by clarifying the mutual relationship of the proteins.

Proteome analysis is an attempt to comprehensively understand various protein-protein relationships supporting the cell functions. While a reasonable methodology meeting the object is being developed, even clarification (identification) of a group of constituent component proteins involved in certain, particular metabolic reaction accompanies many difficulties in the situation now stands. Thus, comprehensive and prompt understanding of changes in proteome, which is an assembly of highly diverse proteins, is desired.

SDS-gel electrophoresis, which is conventionally used for separation of proteins, shows high separability of molecular weights. On the other hand, isoelectric focusing that performs separation based on electric charge of proteins has overcome technical problems, but has difficulty in sample preparation. While two-dimensional electrophoresis, which is a separation technique having features of both in, combination is currently one of the most superior methods in terms of separability of proteins, it has problems in reproducibility. To overcome the problems, a method using multicolor fluorescence labeling in combination, which is what is called the DIGE method, has been developed and practiced. Although automation is difficult for this method, the difficulty in ensuring reproducibility and quantitativeness has been overcome to some extent.

On the other hand, a large-scale protein identification system has been developed wherein liquid chromatography, mass spectrometer and data analysis system are connected, and the process from separation of samples to identification of protein is consistently performed automatically online. Since this system shows extremely high sensitivity and enables extremely accurate mass measurement of even a small amount of a sample, a target protein can be often identified by measuring the mass of only 2 or 3 kinds of peptide fragments derived from the protein. Alternatively, it is also possible to directly determine the amino acid sequence of a peptide by mass spectrometry and identify the protein from the amino acid sequence.

In addition, changes in the level of protein in the cells or tissues between normal ones and pathologic ones, or the level of protein expressed in the tissues with various diseases including tissue and brain under development, or tissues with altered function due to genetic mutation provide an important tip for the elucidation of pathology. Consequently, the demand not only for the technique for identifying intracellular proteins but also the technique for protein quantification is increasing.

Conventionally, the amount of a target protein has been relatively determined by indirectly detecting the binding of an antibody that specifically binds to the target protein. In this method, the target protein needs to be identified beforehand and an antibody capable of detecting the protein needs to have been obtained.

On the other hand, a method of analyzing the abundance ratio has also been used at present, which includes producing a difference in the mass of the same protein between samples using isotopes and subjecting the protein to mass spectrometry. This method is advantageous in that an unidentified protein can be identified and quantified by a single run of the analysis. For this method, labeling reagents such as ICAT (registered trade mark) reagent, iTRAQ (registered trade mark) reagent, ICPL (registered trade mark) reagent, NBS (registered trade mark) reagent and the like are utilized (see, for example, patent document 1). Moreover, many designs have been employed as evidenced by a method including allowing a digestion enzyme to independently act on samples to be compared in two kinds of water containing light oxygen atom and heavy oxygen atom, whereby peptides having mass difference of 2 are produced since oxygen is introduced as OH of carboxylic acid newly produced, and separating them by mass spectrometry to determine the quantitative ratio, a method including culturing cells with amino acids containing a light atom and a heavy atom of C, N to constitute total proteins with the amino acids, and investigating the abundance ratio of the components of the both and the like.

Among the aforementioned labeling reagents, ICAT reagent and NBS reagent are associated with various, defects. For example, it may be difficult to perform analysis depending on kinds of proteins, since these reagents bind to amino acid residues of cysteine and tryptophan, respectively, which are small in contents in proteins. In addition, comparison is limited between two kinds of samples. In addition, iTRAQ reagent and ICPL reagent used for labeling an amino group of a lysine residue of a protein are difficult to preserve, since an amide bond is formed using unstable activated carboxylic acid. Furthermore, these four kinds of reagents are all expensive, which is also a factor limiting the use thereof.

patent document 1: JP-A-2003-107066

SUMMARY OF THE INVENTION

The present invention has been made in view of the aforementioned problems of conventional protein quantification techniques, and is not largely different from prior art in the main purpose of providing a protein analysis method capable of obtaining identification and quantitative information of a protein by simpler processing. However, the present invention aims to provide a protein analysis method superior in the function, convenience and economy, and a kit used therefor.

In an attempt to solve the aforementioned problems, the present inventor has taken note and conducted intensive studies of a protein analysis method comprising identifying and quantifying a target peptide by a mass spectrometer, and found that a combination of stable isotopes of a pyrylium derivative, which is the compound to be used in the present invention, is highly useful as a labeling compound for quantification of a protein by mass spectrometry, which resulted in the completion of the present invention.

Accordingly, the present invention provides the following.

[1] A protein analysis method comprising comparing two or more kinds of protein-containing samples using a mass spectrometer, and analyzing the quantitative ratio of the same kind of protein contained in each sample, wherein a combination of two or more kinds of stable isotopes of a compound represented by the formula (I):

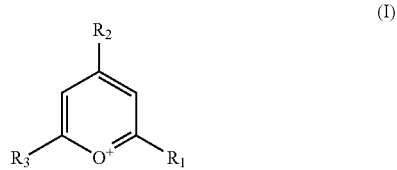

(I)

wherein $R_1$, $R_2$ and $R_3$ are the same or different and each is hydrogen, halogen or alkyl, or a salt thereof is used as a labeling compound to produce a difference in the mass of the same kind of protein contained in each sample.

[2] The method of [1], wherein the compound of the formula (I) is 2,4,6-trimethyl pyrylium.

[3] The method of [1], wherein the mass difference between stable isotopes contained in the aforementioned combination is two or more.

[4] A reagent kit used for comparing two or more kinds of protein-containing samples using a mass spectrometer, and analyzing the quantitative ratio of the same kind of protein contained in each sample, which comprises, as a labeling compound, a combination of two or more kinds of stable isotopes of a compound represented by the formula (I):

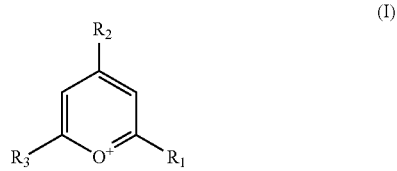

(I)

wherein $R_1$, $R_2$ and $R_3$ are the same or different and each is hydrogen, halogen or alkyl, or a salt thereof.

[5] The kit of [4], wherein the compound of the formula (I) is 2,4,6-trimethyl pyrylium.

[6] The kit of [4], wherein the mass difference between stable isotopes contained in the aforementioned combination is two or more.

[7] The method of any of [1]-[3], wherein the quantitative ratio is determined by labeling an internal standard sample containing a protein to be subjected to mass spectrometry with one of the stable isotopes of the aforementioned labeling compound, and determining the ratios of MS spectrum intensity derived from the protein-containing samples to MS spectrum intensity derived from the internal standard sample.

According to the protein analysis method of the present invention, quantitative information of a protein can be obtained by simple processing. The present invention also provides a kit to be utilized for the protein analysis method.

DETAILED DESCRIPTION OF THE INVENTION

Figure 1:
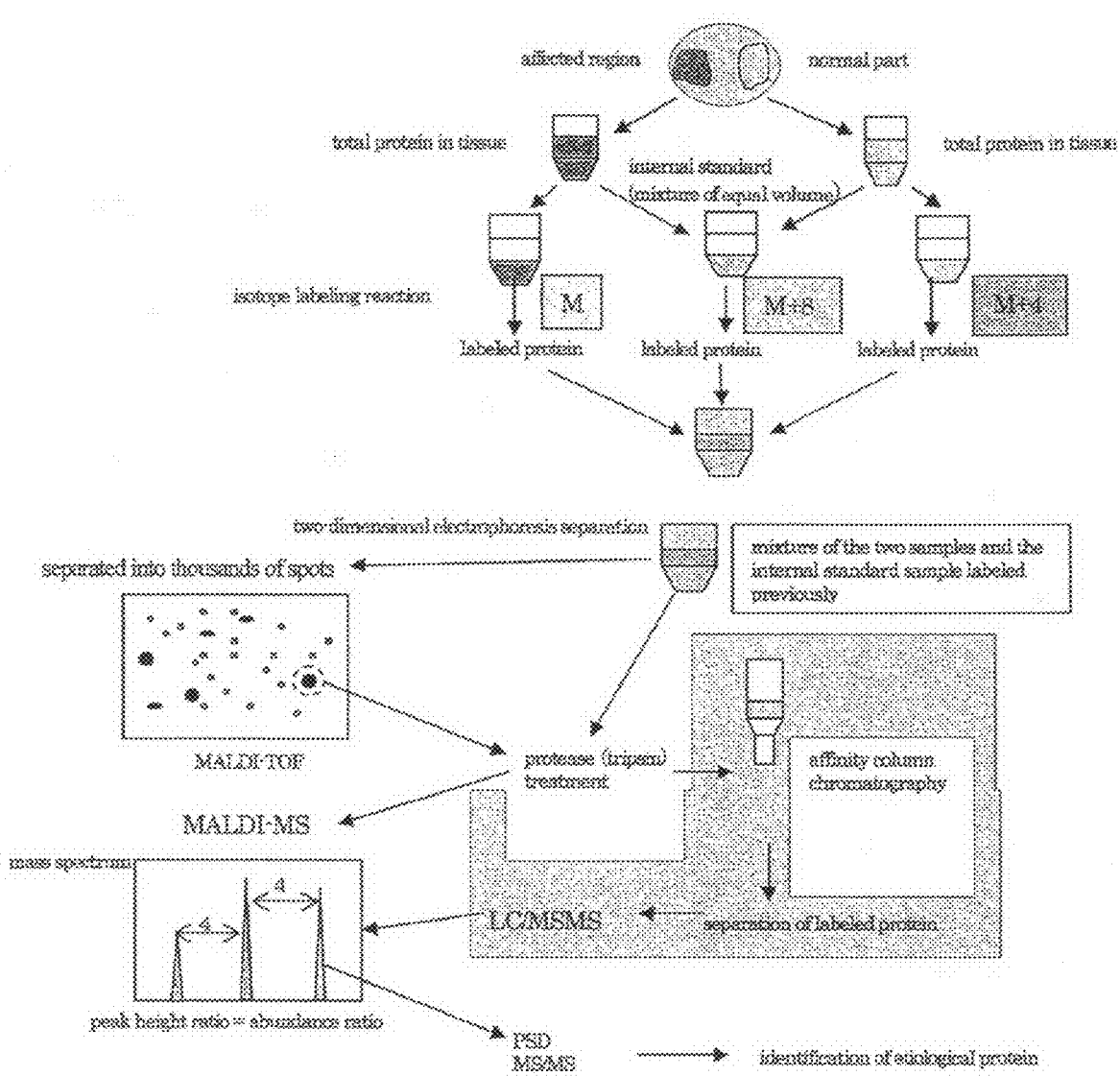
FIG. 1 shows the flow of a protein quantification method using an internal standard sample.

The present invention relates to a protein analysis method, comprising comparing two or more kinds of protein-containing samples using a mass spectrometer, and analyzing the quantitative ratio of the same kind of protein contained in each sample. The present invention particularly provides a protein analysis method, comprising producing a difference in the mass of the same kind of protein contained in each sample by using a combination of two or more kinds of stable isotopes of the compound represented by the above-mentioned formula (I) or a salt thereof (hereinafter they are also referred to simply as the compound in the present invention) as a labeling compound.

In the formula (I), $R_1$, $R_2$ and $R_3$ are the same or different and each is hydrogen, halogen or alkyl. $R_1$, $R_2$ and $R_3$ are each preferably hydrogen, halogen, or alkyl having a carbon number of 1-6 (e.g.,-methyl, ethyl, propyl, isopropyl, butyl, sec-butyl, isobutyl, tert-butyl, pentyl, hexyl etc.), more preferably alkyl having a carbon number of 1-3 (e.g., methyl or ethyl). Examples of the aforementioned halogen include fluorine, chlorine, bromine, iodine and the like.

Preferable examples, of the compound of the formula (I) include 2,4,6-trimethyl pyrylium, 2-ethyl-4,6-dimethyl pyrylium, 2,6-diethyl-4-methyl pyrylium and the like.

The compound of the present invention is generally used in the form of a salt. In this case, the salt consists of the compound of the formula (I) and any anion atom or anion molecule. Examples of the anion atom or anion molecule include anions such as an anion from hexafluorophosphoric acid, trifluoromethanesulfonic acid, tetrafluoroboric acid or the like. While the kind thereof is not subject to any particular limitation as long as it does not inhibit the labeling reaction of protein, it is preferably an anion from tetrafluoroboric acid.

Therefore, preferable examples of the compound in the present invention include 2,4,6-trimethyl pyrylium tetrafluoroborate, 2-ethyl-4,6-dimethyl pyrylium tetrafluoroborate salt, 2,6-diethyl-4-methyl pyrylium tetrafluoroborate and the like.

In the present invention, a protein or a peptide contained in each sample is labeled with stable isotopes of the compound in the present invention, which have different masses, whereby the same kind of protein or peptide has mass difference. While the mass difference between stable isotopes to be used is not particularly limited as long as the same kind of protein or peptide having a mass difference can be separated by a mass spectrometer, it is generally two or more, preferably 3 or more. The upper limit of the mass difference is not particularly limited as long as the compound in the present invention can exist stably. Generally, since the mass difference between compounds is produced by a mass difference between $^{12}C$ and $^{13}C$, the upper limit of the mass difference is the same as the number of carbon atoms contained in the compound in the present invention.

The compound in the present invention can be synthesized according to the methods taught in, for example,
1) Balaban, A. T., Boulton A. J., Organic Synthesis, Coll., vol. 5, p. 1112 (1973); vol. 49, p. 121 (1969).
2) Balaban, A. T., Boulton A. J., Organic Synthesis, Coll., vol. 5, p. 1114 (1973)
3) Ghiviriga I., Czerwinski E. W., Balaban A. T., Croatia Chemica Acta, vol. 77(1-2), p. 391-396 (2004)
and the like.

Now, the three compounds recited above, 2,4,6-trimethyl pyrylium tetrafluoroborate salt, 2-ethyl-4,6-dimethyl pyrylium tetrafluoroborate salt and 2,6-diethyl-4-methyl pyrylium tetrafluoroborate salt, are taken as examples in the explanation of preferable stable isotopes used as labeling compounds.

One example of the combination of three preferable kinds of stable isotopes of 2,4,6-trimethyl pyrylium tetrafluoroborate salt is shown in the formula (II):

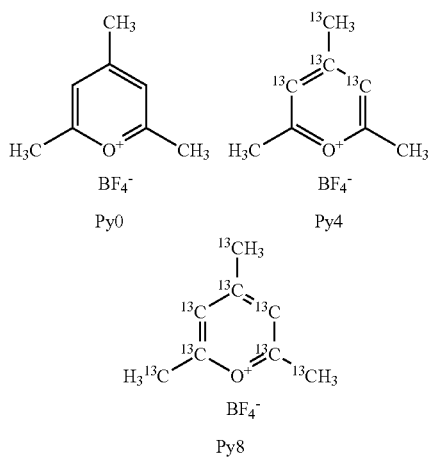

Note that the position of carbon atom replaced with $^{13}C$ may be any, and a carbon atom at the position other than that shown in the formula (II) is optionally replaced with $^{13}C$ as long as the number of $^{13}C$ atom contained in each compound is not changed. 2 or 3 kinds selected from the above-mentioned 3 kinds of compounds can be used in combination for the method of the present invention. Hereinafter each isotope is indicated as Py0, Py4 or Py8 as shown in the formula (II), and the isotopes are to be generically referred to as Py compound. In the formula (II), the carbon atom with the number 13 on the left shoulder of C is a carbon atom having a mass number of 13. That is, any carbon of a labeling compound having the lowest mass (chemical formula (Py0)) has a mass number of 12, and in a labeling compound having an intermediate mass number (chemical formula (Py4)), 4 out of 8 carbon atoms having a mass number of 12 are replaced with a carbon atom having a mass number of 13. In the third isotope compound (chemical formula (Py8)), any carbon atom of Py0 is replaced with a carbon atom having a mass number of 13. Therefore, the relationship of mass difference among the 3 kinds of labeling compounds is Py0, Py0+4 (=Py4), Py0+8(=Py8). In addition, the mass difference among the aforementioned stable isotopes in these Py compounds is 4.

Similarly, one example of the combination of four preferable kinds of stable isotopes of 2-ethyl-4,6-dimethyl pyrylium tetrafluoroborate salt is shown in the formula (III):

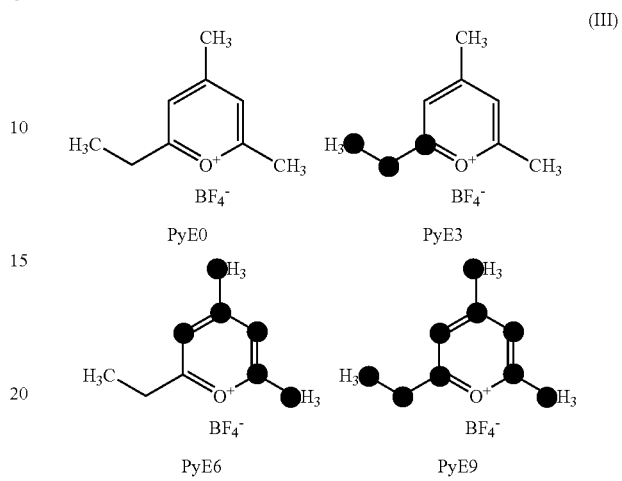

Note that the position of carbon atom replaced with $^{13}C$ may be any, and the carbon atom at the position other than that shown in the formula (III) is optionally replaced with $^{13}C$ as long as the number of $^{13}C$ atom contained in each compound is not changed. 2, 3 or 4 kinds selected from the above-mentioned 4 kinds of compounds can be used in combination for the method of the present invention. Hereinafter each isotope is indicated as PyE0, PyE3, PyE6 or PyE9 as shown in the formula (III), and the isotopes are to be generically referred to as PyE compound. In the formula (III), the black circle is a carbon atom having a mass number of 13. That is, any carbon of a labeling compound having the lowest mass (chemical formula (PyE0)) has a mass number of 12, and in a labeling compound having the second mass number (chemical formula (PyE3)), 3 out of 9 carbon atoms having a mass number of 12 are replaced with a carbon atom having a mass number of 13. In the third labeling compound (chemical formula (PyE6)), any $^{12}C$ in PyE3 is replaced with $^{13}C$, and any $^{13}C$ in PyE3 is replaced with $^{12}C$, and in the fourth labeling compound (chemical formula (PyE9)), any carbon atom of PyE0 is replaced with $^{13}C$. Therefore, the relationship of mass difference among the 4 kinds of labeling compounds is PyE0, PyE0+3(=PyE3), PyE0+6(=PyE6), PyE0+9 (=PyE9). In addition, the mass difference among the aforementioned stable isotopes in these PyE compounds is 3-9.

Similarly, moreover, one example of the combination of four preferable kinds of stable isotopes of 2,6-diethyl-4-methyl pyrylium tetrafluoroborate salt is shown in the formula (IV):

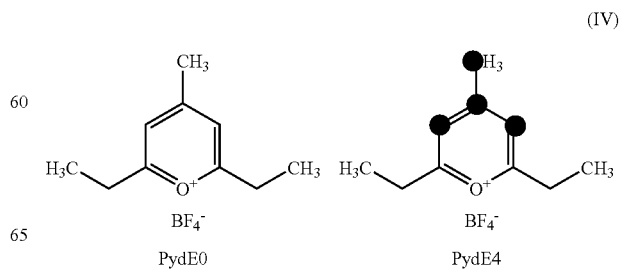

-continued

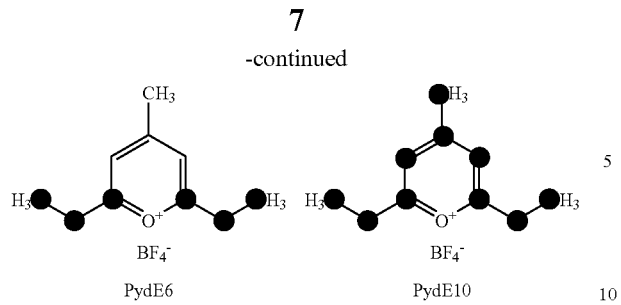

PydE6    PydE10

Note that the position of carbon atom replaced with $^{13}C$ may be any, and the carbon atom at the position other than that shown in the formula (IV) is optionally replaced with $^{13}C$ as long as the number of $^{13}C$ atom contained in each compound is not changed. 2, 3 or 4 kinds selected from the above-mentioned 4 kinds of compounds can be used in combination for the method of the present invention. Hereinafter each isotope is indicated as PydE0, PydE4, PydE6 or PydE10 as shown in the formula (IV), and the isotopes are to be generically referred to as PydE compound. In the formula (IV), the black circle is a carbon atom having a mass number of 13. The relationship of mass difference among the 4 kinds of labeling compounds is PydE0, PydE0+4(=PydE4), PydE0+6 (=PydE6), PydE0+10(=PydE10). In addition, the mass difference among the aforementioned stable isotopes in these PydE compounds is 2-10.

In the above-mentioned Py compound, PyE compound and PydE compound, the position of the carbon atom having a mass number of 13 was logically induced from the synthesis process, and the mass number was confirmed by a mass spectrometry apparatus.

A protein or peptide can be labeled with the compound in the present invention according to a well-known method described in, for example, the following publication: Craig D. B., Wetzl B. K., Duerkop A., and Wolfbeis O. S., Electrophoresis, vol. 26, p. 2208-2213 (2005) and the like.

In addition, the compound in the present invention binds to an ε-amino group of a lysine residue of a protein or peptide by, for example, the following reaction:

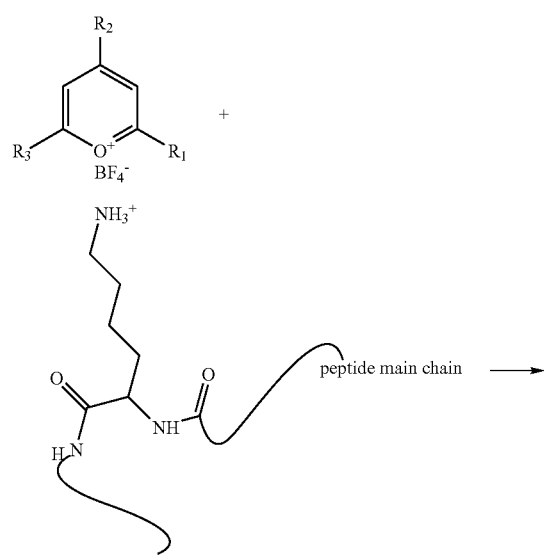

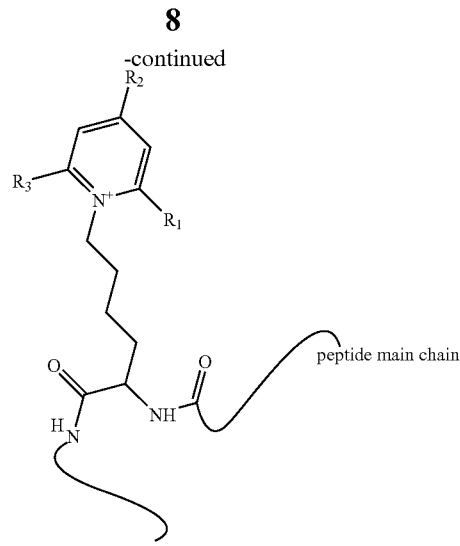

In a rare case, it reacts with an α-amino group. By this reaction, the compound in the present invention labels a protein or peptide.

In the present specification, the term peptide refers to one containing several to more than dozen amino acids. As well known in the art, for identification and quantification of a target protein, a peptide obtained by digesting the protein with protease is generally subjected to mass spectrometry.

The advantage of utilizing the compound in the present invention as a label is, for example, as follows. That is, the aforementioned labeling reaction is mild and rapid; the aforementioned labeling reaction forms a quaternary amine, which does not affect the electric charge of the target protein, and therefore, the subsequent electrophoresis separation is possible; the compound in the present invention can be preserved at room temperature; a solution of the compound in the present invention is also stable at room temperature; and the like. In addition, as with the case of, for example, the aforementioned Py compound, PyE compound and PydE compound, since a combination of 3 or more kinds of stable isotopes of the compound in the present invention can be used as a labeling compound, the maximum number of samples to be compared is generally 3 kinds or more, which provides high efficiency in the quantitative ratio analysis of the same kind of protein in multiple kinds of samples. Furthermore, the compound in the present invention is advantage in that the cost per sample is low as compared to the aforementioned reagents (ICAT reagent, NBS reagent, iTRAQ reagent and ICPL reagent) used for protein mass spectrometry.

The method of the present invention includes producing a mass difference in the same kind of protein contained in each sample by using a combination of two or more kinds of stable isotopes of the compound in the present invention as a labeling compound in two or more kinds of protein-containing samples to be compared. The labeled same kind of protein shows no difference in the chemical properties between samples, but shows difference only in the mass number. As mentioned below, therefore, the same kind of peptide can be separated from other kind of peptide by separation based on chemical properties (for example, liquid chromatography, SDS-PAGE or two-dimensional electrophoresis), and the same kind of peptide can be separated from one another based on the mass difference by subsequent mass spectrometry.

Examples of the aforementioned two or more kinds of protein-containing samples include two kinds of samples collected from a sample of a healthy state and a sample of a disease state of the same kind of biological tissue, samples derived from a certain kind of cell culture in various developmental stages, and the like.

When the method of the present invention is practiced, simultaneous identification and quantification of a protein using a tandem mass spectrometer is general assumed. Examples of the mass spectrometer to be used for the method of the present invention include a quadrupolar time-of-flight tandem mass spectrometer (MS/MS), a Fourier-transform mass spectrometer (FT-MS) and the like. The apparatus configuration thereof may be similar to the conventional ones.

The protein analysis using the compound in the present invention can be performed according to the procedures well known to those of ordinary skill in the art. General procedures for quantifying a protein utilizing the method of the present invention are simply explained in the following. While the number of the kind of the protein-containing sample to be compared is not indicated in the following explanation, samples up-to-the number of the kind of stable isotopes used for the labeling can in fact be compared and, furthermore, using the below-mentioned internal standard method, any number of the kind of samples can be substantially compared.

Quantification of protein utilizing the method of the present invention generally includes the following steps:

step 1) a step comprising labeling each of protein-containing samples to be compared with the compound in the present invention having a different mass number due to isotope, thereby producing a difference in the mass of the same kind of protein contained in each protein-containing sample;

step 2) a step comprising mixing respective samples containing isotope-labeled protein;

step 3) a step comprising optionally separating proteins in the mixture of step 2 from each other, and cleaving the protein with a restriction enzyme at a particular amino acid site to give a sample containing isotope-labeled peptides; and step 4) a step comprising measuring MS spectrum of the aforementioned isotope-labeled peptides, determining MS spectrum intensity of each of the same kind of peptide having mass difference due to isotope labeling, and determining quantitative ratio of the protein based on the intensity ratio.

Each of the aforementioned steps is explained in detail in the following. However, the following explanation is not to be construed as limiting the embodiments of the present invention. General flow of the method of the present invention is shown in FIG. 1, which is offered for appropriate reference to ensure better understanding. In the analysis of FIG. 1, a protein in 3 kinds of samples consisting of a protein-containing sample derived from an affected region (labeled with the aforementioned Py0 compound (mass M)), a protein-containing sample derived from a normal part (labeled with the aforementioned Py4 compound (mass M+4)) and an internal standard sample prepared therefrom (labeled with the aforementioned Py8 compound (mass M+8)) is quantified.

In step 1, the labeling is performed, for example, as follows. That is, the SH group of total protein in a sample to be analyzed is reduced and alkylated in advance, the compound in the present invention is added under basic conditions to a protein-containing sample dissolved in a suitable solvent (e.g., urea containing Tris-HCl buffer), and the mixture is instantaneously mixed to allow reaction. The reaction may be completed in 30 min at room temperature, or continued for up to 12 hr to increase labeling efficiency.

In step 2, respective protein-containing samples labeled in step 1 are mixed. Unreacted labeling compounds are removed by gel filtration method or protein precipitation reagent, and labeled proteins are collected and concentrated.

Step 3 largely follows either of the following two methods:
(a) the aforementioned protein mixture is roughly separated by one-dimensional gel separation, two-dimensional gel separation or suitable chromatomedia and the like, and the resulting protein is hydrolyzed with protease to liberate peptides; and
(b) the aforementioned protein mixture is directly degraded with protease, without previously subjecting the contained protein to gel separation or development by chromatography for separation from each other as in (a).

For protein degradation, besides trypsin of the primary selection, Arg peptidase, Glu peptidase and the like are used as the secondary selection; however, Lys endopeptidase is not used.

The flow after liberation of peptides to mass spectrometry of peptides is as follows. That is, The labeled peptides and unlabeled peptides liberated from the protein separated by the operation in (a) may sometimes be directly subjected to mass spectrometry by MALDI-TOF/MS, without a peptide separation operation. It is also possible to separate peptides by liquid chromatography and subject the peptide to ESI/MS/MS analysis.

On the other hand, the peptides liberated by the operation in (b) is separated by a two-dimensional separation such as one wherein one-dimensional separation is performed with an SCX column, and the eluted components are separated using a second reversed-phase resin column, and introduced into ESI/MS/MS, whereby relative intensity of the labeled peptide and the amino acid sequence information thereof are obtained by a single analysis.

Here, while the molecular weight of the peptides to be used for the measurement of MS spectrum in the next step is not particularly limited, in consideration of the decreased analysis precision due to an influence of naturally occurring isotope, the molecular weight is preferably 1000-3000, more preferably 1500-2000. Therefore, step 3 preferably includes isolation of peptide having a molecular weight in the above-mentioned range from protease degradation products.

Then, MS spectra derived from the peptides obtained in the previous step can be obtained using a well-known analysis technique. Since different masses are given to the same kind of peptides derived from different samples by the isotope labeling, said peptides derived from different samples appear as peaks separated from each other in the aforementioned MS spectral data. Thus, the quantitative ratio of the aforementioned peptide between samples, namely, quantitative ratio of the aforementioned proteins between samples, is determined by comparison of the intensity of such separated peaks.

However, for comparison of peak intensity from the aforementioned MS spectrum data, the quantitative ratio needs to be corrected by removing the overlap with the isotope peak of peptide due to naturally occurring isotope, as taught in, for example, JP-A-2005-181011.

Furthermore, it is also possible to identify the aforementioned protein by adding following the aforementioned steps 1-4, the following steps:

step 5) a step comprising selecting, by referring to the MS spectrum in step 4, a peptide whose amino acid sequence is to be determined from respective peptides, and assessing the amino acid sequence of the peptide based on the MS/MS spectrum of the product ion generated from the peptide; and step 6) a step comprising identifying, from known DNA sequences, the corresponding protein based on the amino acid sequence of the aforementioned peptide.

The protein can be identified by a well-known method according to the procedures shown in steps 5 and 6.

In one embodiment of the present invention, a protein analysis method, which is the aforementioned protein analysis method of the present invention, is also provided, wherein the quantitative ratio is determined by labeling an internal standard sample containing a protein to be subjected to mass spectrometry with one of the stable isotopes of the compound in the present invention, and determining the ratios of MS spectrum intensity derived from the protein-containing samples to MS spectrum intensity derived from the internal standard sample.

In the present specification, the term "internal standard sample" refers to a sample utilized for the analysis of the quantitative ratio of the same kind of protein in samples, by comparing the level of the protein in respective samples other than internal standard sample and the level of the protein in the internal standard sample to determine the relative value of contents in respective samples, comparing the relative values among samples, and determining the quantitative ratio of the protein in all samples to be analyzed.

For the above-mentioned object, the internal standard sample preferably contains any protein present in the samples to be analyzed. Therefore, for example, an internal standard sample is prepared as shown below. That is, starting samples with the same total protein content are prepared from all the corresponding protein-containing samples to be analyzed, and equal amounts of the starting samples are mixed.

For protein analysis using an internal standard sample, the internal standard sample is also labeled with one of the stable isotopes of the compound in the present invention, and subjected to the aforementioned protein analysis method of the present invention together with other protein-containing samples to be analyzed.

Using an internal standard sample, samples in a number greater than the number of the kind of stable isotopes of a labeling compound used for the method of the present invention can be quantified. Utilizing an internal standard sample, moreover, protein content can be compared with high precision among plural samples.

Figure 2:
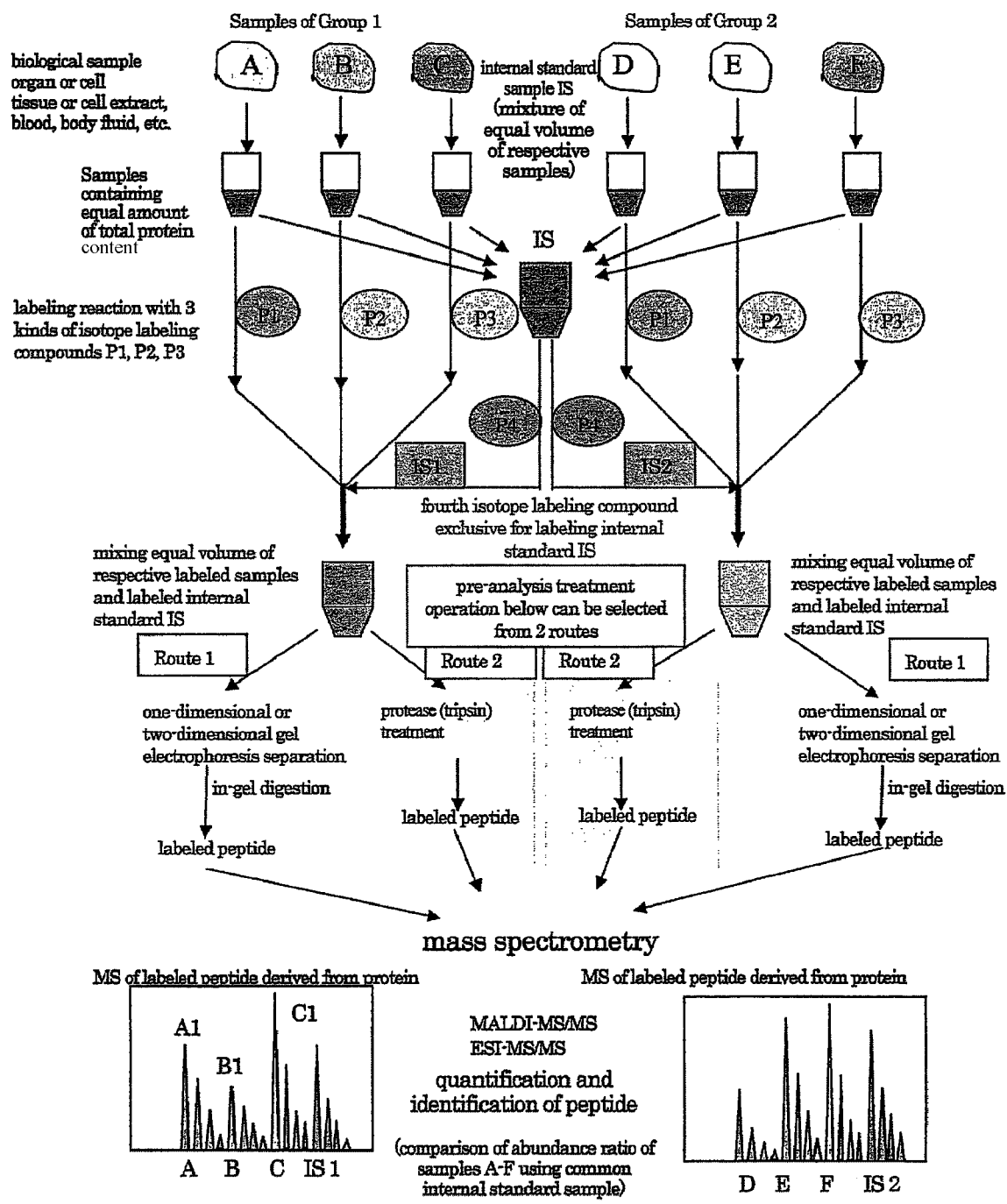
FIG. 2 shows the flow of a quantification method of a protein in many kinds of samples using an internal standard sample.

FIG. 2 shows one example of procedures for analyzing quantitative ratio of the same kind of protein among many kinds of samples. In the analysis of FIG. 2, the number of samples is 6 and the number of the combined stable isotopes used for labeling is 4, for convenience of explanation.

First, an internal standard sample (indicated as IS in FIG. 2) is prepared from 6 kinds of samples in the same manner as above. The 6 kinds of samples are divided into group 1 (containing samples A, B, C) and group 2 (containing samples D, E, F), each consisting of 3 kinds of samples. According to the aforementioned procedures, MS spectrum of a peptide derived from a target protein is measured for each group. The obtained as a result thereof is the MS spectrum as in the lower part of FIG. 2. As mentioned above, the MS spectrum of the labeled peptide is complicated since it varies by one mass, reflecting the abundance ratio of natural isotope in the peptide, and requires correction. Spectrum with maximum intensity after the aforementioned correction (for example, A1, B1 and C1 in FIG. 2, after the aforementioned correction) is free of an influence of natural isotope and reflects the amount of peptide present. To set the MS spectrum intensity of a labeled peptide derived from the internal standard sample as a common comparison standard in the analysis of each group, an equal amount of the internal standard sample is added for every analysis during preparation of a mixed sample. Since the MS spectrum intensity of a peptide derived from the internal standard sample is theoretically the same in the measurement of both groups, the intensity of A, B and C after the aforementioned correction is normalized by the intensity of IS1 after the aforementioned correction, and similarly, the intensity of D, E and F after the aforementioned correction is normalized by the intensity of IS2 after the aforementioned correction. As a result, they are normalized by a common standard and can be compared with each other. The quantitative ratio of the target protein among 6 kinds of samples can be determined from such comparison.

Since a combination of 3 or more kinds of stable isotopes of the compound in the present invention can be used as a labeling compound, it is clear that the compound shows remarkably improved efficiency as compared to a labeling compound of only two kinds of stable isotopes, in an analysis of the quantitative ratio of the same kind of protein among many kinds of samples, utilizing an internal standard sample. Therefore, the method of the present invention is highly useful when an exhaustive proteomics analysis of other kinds of samples is necessary, for example, in the following use:

(1) discovery and variability-analysis of marker proteins for a disease in clinical samples of many patients (clinical test);
(2) comprehensive comparison analysis of abundance ratio of protein expressed in various human and animal tissues (biochemical);
(3) analysis of time-series variation of abundance of protein expressed in cells after administration of a pharmaceutical agent to cultured cells and animal; and
(4) detailed analysis of time-series variation of protein expressed in the developmental stage (developmental engineering), and the like.

In another aspect, the present invention also provides a reagent kit used for the aforementioned protein analysis method, which comprises, as a labeling compound, a combination of two or more kinds of stable isotopes of a compound represented by the formula (I) or a salt thereof. The definitions relating to the compound represented by the formula (I) or a salt thereof, stable isotopes and embodiment of combination are as mentioned above.

Examples of the compound of the formula (I) to be contained in the aforementioned kit include:

(a) a combination of 2 or 3 kinds selected from the aforementioned Py0 compound, Py4 compound and Py8 compound;
(b) a combination of 2, 3 or 4 kinds selected from the aforementioned PyE0 compound, PyE3 compound, PyE6 compound and PyE9 compound; and
(c) a combination of 2, 3 or 4 kinds selected from the aforementioned PydE0 compound, PydE4 compound, PydE6 compound and PydE10 compound.

In one embodiment of the present invention, the compound of the formula (I) contained in the aforementioned kit is 2,4,6-trimethyl pyrylium.

In another embodiment of the present invention, the mass difference between stable isotopes contained in the aforementioned combination in the aforementioned kit is two or more.

The aforementioned kit may contain, besides the aforementioned combination of stable isotopes, one or more kinds of proteases, reaction buffers, wash solutions, or other components necessary or preferable for the combined use with the compound in the present invention. Also, the aforementioned kit optionally contains an instruction manual. Moreover, the kit of the present invention may further contain a reagent for removing unreacted components (wash reagent), a restriction enzyme, a column for peptide purification, a purification solvent and the like.

The contents disclosed in any publication cited in the present specification, including patents and patent applications, are hereby incorporated in their entireties by reference, to the extent that they have been disclosed herein.

The present invention is explained in more detail in the following by referring to Examples, which are not to be construed as limitative.

EXAMPLES

Example 1

LC/MS Analysis of Isotope-labeled HAS

HSA (Human Serum Albumin), which is one kind of human serum protein, was labeled in advance with the aforementioned isotope labeling compounds Py0, Py4 and Py8 (Py compound). Py compound was synthesized according to the synthesis methods described in
1) Balaban, A. T., Boulton A. J. Organic Synthesis, Coll., vol. 5, p. 1112 (1973); vol.49, p.121 (1969).
2) Balaban, A. T., Boulton A. J., Organic Synthesis, Coll., vol. 5, p. 1114 (1973)
3) Ghiviriga I., Czerwinski E. W., Balaban A. T., Croatia Chemica Acta, vol. 77(1-2), p. 391-396 (2004). That is, to a mixed solution of acetic anhydride (13 mmol) and t-butanol (1 mmol) was added dropwise tetrafluoroboric acid (0.95 mmol), and the mixture was reacted while keeping heat generation from exceeding 90° C. The reaction mixture was cooled to room temperature to give precipitated crude crystals, which were purified by recrystallization from methanol. The obtained crystals were applied to an ODS column and purified by water-acetonitrile gradient elution. In the same manner as in the aforementioned method, isotope label Py4 was synthesized from t-butanol $^{13}C4$ wherein all carbon atoms are replaced with $^{13}C$ [synthesized from $^{13}C3$ acetone and $^{13}C1$ methyl iodide (purchased from Cambridge Isotope Laboratories, Inc., USA: CIL) by Grignard reaction] and $^{12}C$ acetic anhydride, and purified. Py8 was synthesized from $^{13}C4$ acetic anhydride and $^{13}C4$ t-butanol, and purified. HSA (29.2 µg) was dissolved in 6M urea-containing borate buffer (pH 8.5, 50 µL) and, after reduced methylation with 5 mM DTT and 10 mM monoiodoacetamide (total amount 60 µL), divided into three (A, B, C each 20 µL). Py0 was added to A, Py4 was added to B and Py8 was added to C, each at 1 mM, and the mixtures were reacted at 55° C. for 30 min to allow labeling. After labeling, unreacted reagent was removed with a 2D-CleanUp reagent (GE Healthcare Biosciences). The three kinds of isotope-labeled HAS were mixed at 1:2:0.5 (=Py0-labeled product:Py4-labeled product:Py8-labeled product), and digested with trypsin. The liberated peptides (containing labeled, unlabeled peptides) were analyzed by LC/MS.

Figure 3:
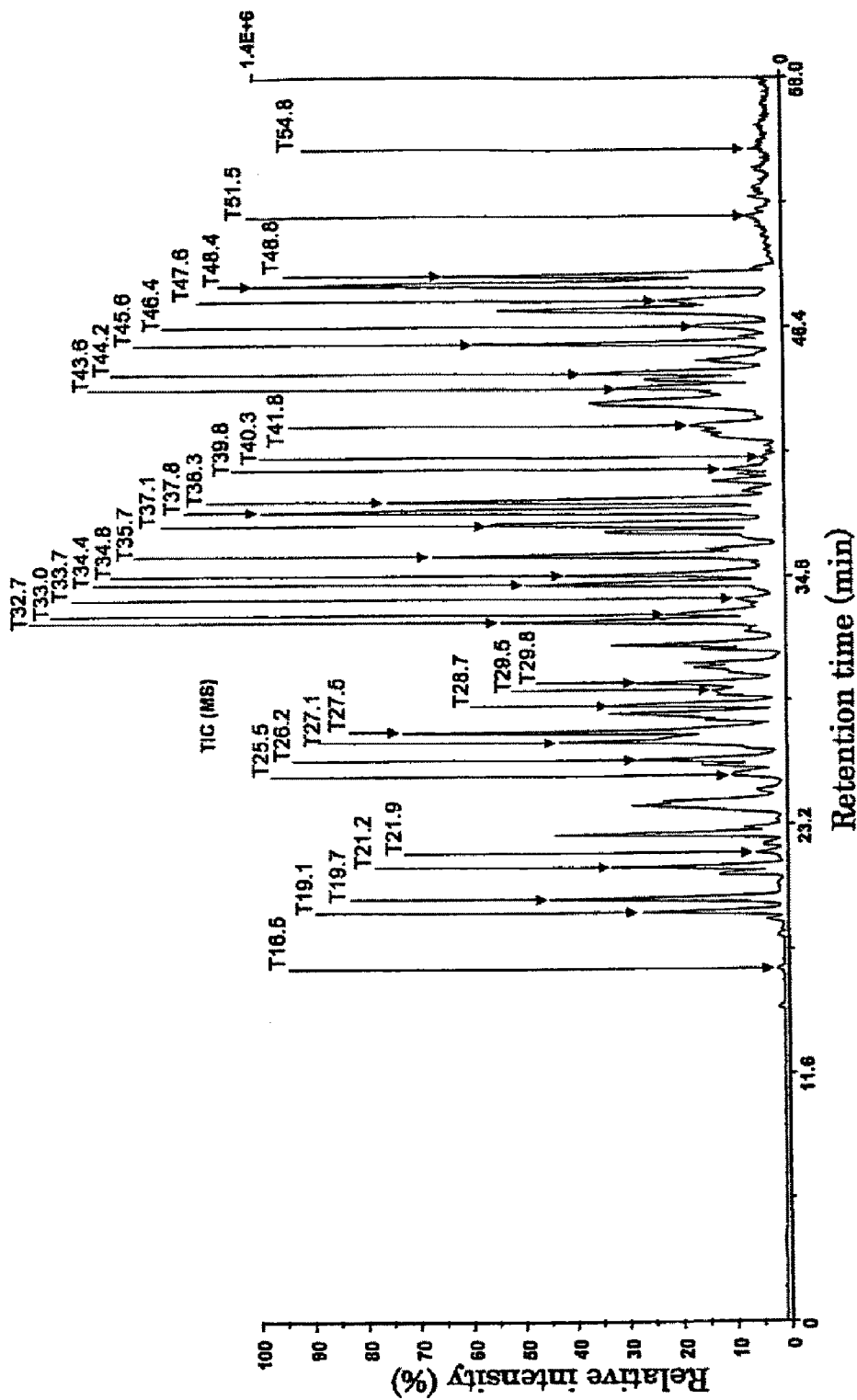
FIG. 3 shows a total ion chromatogram of peptides derived from isotope-labeled products of human serum albumin, wherein the horizontal axis shows retention time (min), and the vertical axis shows relative intensity (%).

FIG. 3 shows a total ion chromatogram of a peptide derived from isotope-labeled HAS, wherein the horizontal axis shows elution time (min) of liquid chromatography (LC), and the vertical axis shows relative intensity (%). Note that peaks correspond to separated peptides, but the same peptide only different in the mass number is contained in the same peak.

Figure 4:
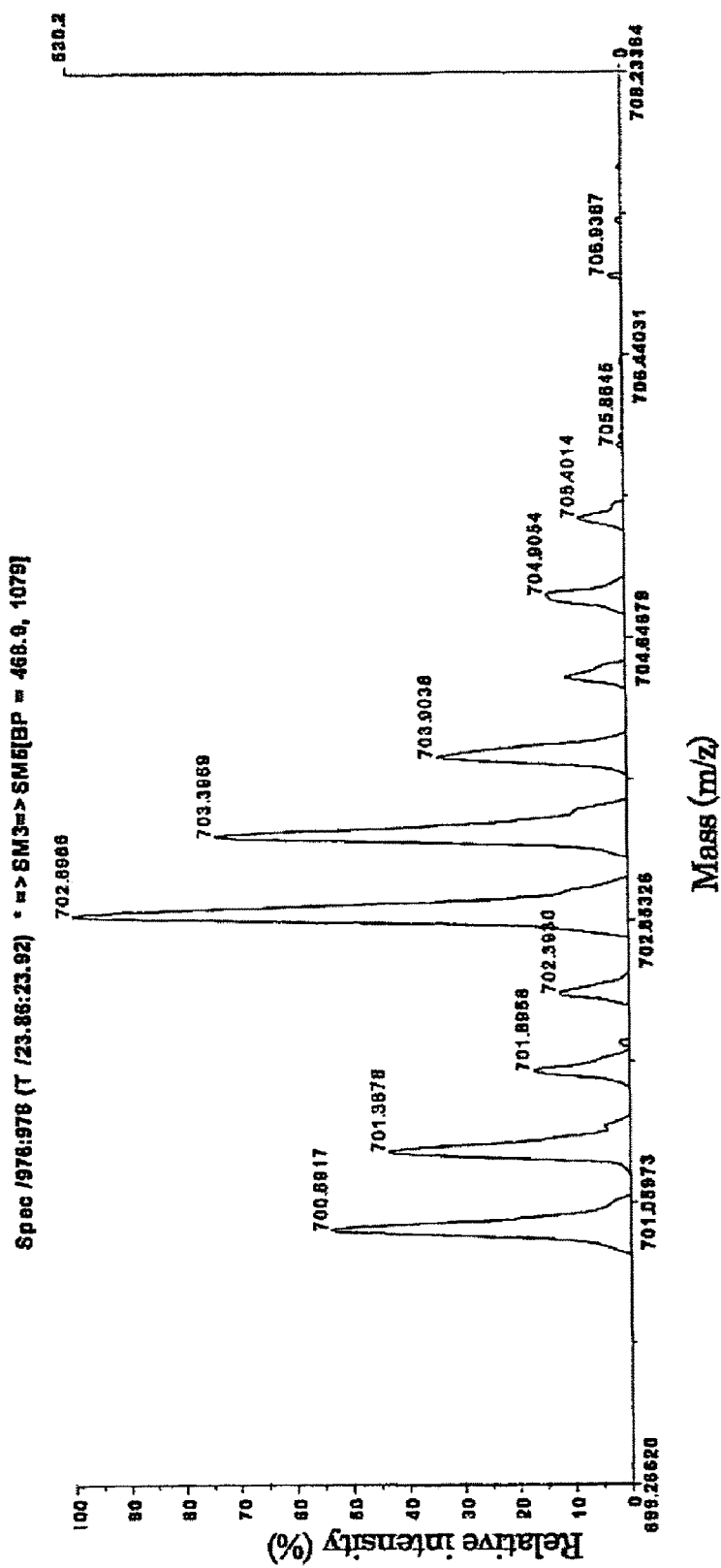
FIG. 4 shows mass spectrometry data of ion during the time from 23.86 min to 23.92 min on the chromatogram of FIG. 3, wherein the horizontal axis shows mass (m/z), and the vertical axis shows relative intensity (%).

FIG. 4 shows the mass spectrometry (MS) data of ion during the time from 23.86 min to 23.92 min on the chromatogram. This corresponds to the mass spectrum of the elution time of the same peptide labeled with isotope labeling reagents Py0, Py4 and Py8. A peptide labeled with Py0 has the smallest mass. Then, the peak of a peptide labeled with Py4 appeared at the position greater by 4 in the mass. Furthermore, the peak of a peptide labeled with Py8 appeared at the position greater by 4 in the mass. The ratio of these peak intensities was the mixing ratio of the 3 kinds of isotope-labeled HAS, which was 1:2:0.5 (=Py0-labeled product:Py4-labeled product:Py8-labeled product). The analysis of the analysis results reaching this conclusion was as follows. A trypsin degradation product of HAS was subjected to by LC/MS analysis, 19 kinds of peptides with a set of Py-labeled 3 kinds of peaks were selected, and the mass distribution was analyzed by a computer software, and the ratio of the peak height was calculated. The result of the average value of all the labeled peptides was 1:2.2 (±0.34):0.55 (±0.27). Plotting the distribution of the peptide molecular weight and the ratio, it was clarified that an accurate ratio (1:2:0.5) was obtained between the molecular weight of 1500-2000, and this range is a preferable practical analysis target range. It was clarified that when the molecular weight exceeds 2000, the spectrum becomes complicated due to an influence of natural isotope element, and even when the number of the mass of the main peak is different by 4, a considerable amount of subpeaks is observed, making it difficult to determine the substantial peak height of the main peak. In general, while valence z of the ion was 3 in many cases by the analysis apparatus used, divalent, tetravalent and pentavalent were also observed.

The subpeak appears within the number of the mass different of 4 due to an influence of naturally occurring isotope. According to the ESI method (electron spray ionization), which is an ionization method, used for the LC/MS analysis, the valence of ion is two or more. This peptide ion is divalent and the actual mass of the peptide is 2-fold of the measurement value. The difference between the values found (700.8917 and 702.8966) multiplied by 2 is 4. The difference between 704.9054 and 702.8966 multiplied by 2 is 4.

The aforementioned results of mass spectrometry reveal that the compound in the present invention is useful for analyzing the quantitative ratio of the same kind of protein contained in two or more kinds of samples.

INDUSTRIAL APPLICABILITY

According to the protein analysis method of the present invention, quantitative information of a protein can be obtained by simple processing. The present invention also provides a kit utilizable for such a protein analysis method.

This application is based on a patent application No. 2007-164249 filed in Japan (filing date: Jun. 21, 2007), the contents of which are incorporated in full herein by this reference.

The invention claimed is:

1. A method for determining the quantitative ratio of a target protein contained in two or more kinds of protein-containing samples using a mass spectrometer, which method comprises:

(i) providing two or more kinds of protein-containing samples to be analyzed;

(ii) preparing an internal standard sample by preparing starting samples with the same total protein content from all the corresponding protein-containing samples to be analyzed, and mixing equal amounts of the starting samples to obtain the internal standard sample;

(iii) labeling the target protein in each of the protein-containing samples to be analyzed and the internal standard sample with a combination of two or more kinds of stable isotopes of a compound represented by the formula (I):

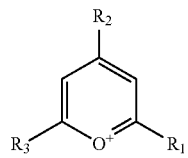

(I)

wherein $R_1$, $R_2$ and $R_3$ are the same or different and each is hydrogen, halogen or alkyl, or a salt thereof having a different mass number due to isotope, thereby producing a difference in the mass of the target protein contained in each of the protein-containing samples and the internal standard sample;

(iv) mixing the respective protein-containing samples and the internal standard sample;

(v) (a) separating the target protein in the mixture obtained in step (iv) from other proteins and cleaving the target protein with a restriction enzyme at a particular amino acid site to give a sample containing isotope-labeled peptides derived from the target protein, or (b) cleaving the target protein in the mixture obtained in step (iv) with a restriction enzyme at a particular amino acid site to give a sample containing isotope-labeled peptides derived from the target protein; and (vi) measuring an MS spectrum of the isotope-labeled peptides derived from the target protein determining an MS spectral intensity of each of the same kind of peptide derived from the target protein having a mass difference due to isotope labeling, determining the ratios of the MS spectral intensity derived from the protein-containing samples to the MS spectral intensity derived from the internal standard sample, determining the quantitative ratio based on the intensity ratios, and correcting the quantitative ratio by removing the overlap with the isotope peak of the peptide due to naturally occurring isotope.

2. The method of claim 1, wherein the compound of the formula (I) is 2,4,6-trimethyl pyrylium.

3. The method of claim 1, wherein the mass difference between stable isotopes contained in said combination is two or more.

4. The method of claim 1, wherein the mass difference between stable isotopes contained in said combination is four or more.

5. The method of claim 1, wherein the salt of the compound represented by the formula (I) is 2,4,6-trimethyl pyrylium tetrafluoroborate salt, and wherein the mass difference between stable isotopes contained in said combination is 4 or 8.

6. The method of claim 1, wherein the two or more kinds of protein-containing samples comprise (i) samples derived from affected and normal region of tissues, or (ii) samples derived from a certain kind of cell culture in various developmental stages.

7. The method of claim 1, wherein the isotope is $^{13}C$ isotope.

* * * * *

UNITED STATES PATENT AND TRADEMARK OFFICE
CERTIFICATE OF CORRECTION

| | | |
|---|---|---|
| PATENT NO. | : 8,071,392 B2 | Page 1 of 1 |
| APPLICATION NO. | : 12/452233 | |
| DATED | : December 6, 2011 | |
| INVENTOR(S) | : Shigeru Matsukawa | |

It is certified that error appears in the above-identified patent and that said Letters Patent is hereby corrected as shown below:

In claim 1, column 15, line 29, "protein" should be --protein,--.

Signed and Sealed this
Third Day of April, 2012

David J. Kappos
*Director of the United States Patent and Trademark Office*